(12) United States Patent
Yamamori et al.

(10) Patent No.: US 6,764,846 B2
(45) Date of Patent: Jul. 20, 2004

(54) BIOJELLY-PRODUCING MICROORGANISM, MICROORGANISM-CONTAINING COATING, MICROORGANISM-CONTAINING COATING FILM

(75) Inventors: Naoki Yamamori, Kyotanabe (JP); Akio Harada, Nara (JP); Nobuki Hayase, Niihama (JP)

(73) Assignee: Nippon Paint Co., Ltd., Osaka (JP)

( * ) Notice: Subject to any disclaimer, the term of this patent is extended or adjusted under 35 U.S.C. 154(b) by 0 days.

(21) Appl. No.: 09/899,212

(22) Filed: Jul. 6, 2001

(65) Prior Publication Data

US 2002/0018764 A1 Feb. 14, 2002

(30) Foreign Application Priority Data

Jul. 7, 2000 (JP) .......................... 2000-206228
Jul. 7, 2000 (JP) .......................... 2000-206229

(51) Int. Cl.$^7$ .............................................. C12N 1/12
(52) U.S. Cl. .................................... 435/252.1; 424/93.4
(58) Field of Search ...................... 424/93.4; 435/252.1

(56) References Cited

FOREIGN PATENT DOCUMENTS

| EP | 0 084 334 | * | 7/1983 |
| EP | 0 702 065 A | | 3/1996 |
| WO | 96 03311 A | | 2/1996 |

OTHER PUBLICATIONS

Raguenes et al., "Alteromonas infernus sp. nov., a new polysaccharide–producing bacterium isolated from a deep–sea hydrothermal vent", J. Applied Microbiology 82 (4) : 422–430 (1997).

Vincent et al., "Production and Characterization of an Exopolysaccharide Excreted by a Deep_Sea Hydrothermal Vent Bacterium Isolated from the Polychaete Annelid Alvinella pompejana", Applied and Environmental Microbiology 60 (11) : 4134–41 (1994).

Samain et al., "Simultaneous Production of two Different Gel–Forming Exopolysaccharides by an Alteromonas Strain Originating from Deep Sea Hydrothermal Vents". Carbohydrate Polymers 34 (4) : 235–41 (1997).

Bozal,Nuria et al "Anew bacterial strain of Antarctica, Alteromonas sp. That produces a heteropolymer slime" Polar Biology, vol. 14, No. 8, 1994, pp. 561–567.

Kon–Ya,K et al "Inhibitory effect of bacterial ubiquinones on the settling of barnacle, Balanus amphitrite" Experientia (Basel), vol., 51, No. 2, 1995, pp. 153–155.

Holmstrom,Carola et al "Marine Pseudoalteromonas species are associated with higher organisms and produce biologically active extracellular agents" Fems Microbiology Ecology, vol., 30, No. 4, Dec. 1999, pp. 285–293.

* cited by examiner

Primary Examiner—Sandra E. Saucier
(74) Attorney, Agent, or Firm—Sughrue Mion, PLLC

(57) ABSTRACT

The present invention provides a microorganism which, when an underwater structure is formed with a coating film containing it, produces a biojelly in water to prevent fouling of the structure with macroscopic aquatic life, such a coating or a coating film, and a method of preventing attachment of macroscopic aquatic life which comprises using said coating or coating film.

The present invention is directed to a strain of microorganism belonging to the genus Alteromonas and having the ability to produce a biojelly.

3 Claims, 1 Drawing Sheet

BIOJELLY-PRODUCING MICROORGANISM, MICROORGANISM-CONTAINING COATING, MICROORGANISM-CONTAINING COATING FILM

TECHNICAL FIELD

The present invention relates to a biojelly-producing strain of microorganism, a coating and a coating film each containing said microorganism, and a method of preventing attachment of macroscopic aquatic life which comprises using said coating or coating film.

BACKGROUND ART

Aquatic creatures, such as barnacles, hard-shelled mussels, algae, etc., tend to attach themselves to underwater structures such as ships and fishnets to cause various troubles, for example inefficient navigation of ships with wastes of fuel or clogging of fishnets and shortening of their useful life.

The surface of an underwater structure is not only inhabited by macroscopic aquatic life, such as barnacles, hard-shelled mussels and algae, but also covered with a thin layer (slime layer) attributable to aquatic microorganisms and products of their metabolisms, and heretofore such a thin layer has been considered to be a fouling matter and removed.

On the other hand, however, there is a reported technology which lands on the fact that underwater structures carrying such thin-film layers are rather hardly receptive to macroscopic aquatic creatures. Japanese Kokai Publication Hei-8-133920 refers to such a thin-film layers not thinner than 0.3 mm as a biojelly and discloses a method of preventing attachment of macroscopic aquatic life which comprises forming such a biojelly on a structural surface.

Japanese Kokai Publication Hei-8-81308 and Japanese Kokai Publication Hei-8-92009 disclose that such a biojelly layer can be formed by coating an underwater structure with a coating containing a cinnamic acid type, silane type or benzylidene-aniline type compound.

SUMMARY OF THE INVENTION

The object of the present invention is to provide a microorganism which, when an underwater structure is formed with a coating film containing it, produces a biojelly in water to prevent fouling of the structure with macroscopic aquatic life, such a coating or a coating film, and a method of preventing attachment of macroscopic aquatic life which comprises using said coating or coating film.

The present invention is directed to a strain of microorganism belonging to the genus Alteromonas and having the ability to produce a biojelly.

The invention is further directed to a coating containing said strain of microorganism.

The invention is further directed to a coating film containing said strain of microorganism.

The invention is further directed to a method of preventing attachment of macroscopic aquatic life to an underwater structure,
which comprises coating the surface of said structure with said coating or forming said coating film on said surface.

DETAILED DESCRIPTION OF THE INVENTION

The present invention is now described in detail.

The inventors of the present invention isolated a strain of microorganism belonging to the genus Alteromonas from the biojelly formed by using a cinnamic acid type, silane type or abenzylidene-aniline type compound as a biojelly-forming agent and found that, when a coating containing said strain of microorganism is used to form a coating film on an underwater structure, the coating film has an antifouling effect to macroscopic aquatic life. The present invention has come forth from the above finding.

In the context of the invention, the term biojelly means a slimy or jelly-like substance produced by some strains of microorganism belonging to the genus Alteromonas, which, when formed on an underwater structure, would prevent attachment of macroscopic aquatic creatures.

The following test can be used to ascertain whether such a biojelly is produced or not. Thus, 1 weight part of a cell suspension of the $3 \times 10^{10}$ cells/ml concentration is mixed with 70 weight parts of a 10 weight % aqueous solution of a polyacrylamide having a molecular weight of 13000, 10 weight parts of ethylene glycol dimethacrylate, and 0.5 weight part of ammonium persulfate, followed by addition of 0.2 weight part of TEMED. This mixture is coated on an acrylic plate, allowed to stand in a nitrogen atmosphere at room temperature for 2 hours, and kept immersed in seawater for 1 month. When a slimy or jelly-like substance is found on the acrylic plate and there is no evidence of macroscopic aquatic life adherent thereto, the particular strain of microorganism is regarded as a biojelly-producing strain.

The term "macroscopic aqueous life" means those organisms which attach themselves to underwater structures and grow in situ to the extent of each individual being distinguishable by the naked eye, thus including such aquatic animals as barnacles, hard-shelled mussels, oysters, hydrozoans, moss worms, ascidians, serupula, etc. and such aquatic plants as sea lettuce, shiomidoro and so on.

The microorganism for use according to the present invention is not particularly restricted as far as it belongs to the genus Alteromonas and is capable of producing a biojelly. As an example, the SHY 1-1 strain can be mentioned. The SHY 1-1 strain is a strain of microorganism which the present inventors isolated from the biojelly formed on a filter when a dish containing benzylidene-aniline powders and covered with the filter was immersed in seawater at 15° C. for 2 weeks and has the property to produce a biojelly with good efficiency.

The SHY 1-1 strain having the morphology depicted in FIG. 1 is a marine non-fermentative Gram-negative rod bacterium which is motile by means of single polar flagella. It grows luxuriantly on nutrient salt media enriched with sodium chloride to the seawater concentration level and produces polysaccharides. The temperature for growth ranges from 5 to 35° C., with the optimum temperature being around 30° C. The pH for growth is pH 3 to 9, with the optimum pH for growth being about neutral. While shake culture and static culture are possible, shake culture is conducive to better growth. In static culture, a thin film suspected to be a biojelly is observed.

The SHY 1-1 strain has the microbiological characteristics shown below in Table 1. In the table, the mol % (G+C) of the intracellular DNA is the value found by HPLC. The symbol NP stands for no characteristic colony pigmentation.

TABLE 1

| Parameter tested | Result |
| --- | --- |
| Morphology | Rods |
| Gram stain | − |
| Sporogenicity | − |
| Motility | + |
| Flagella | Polar |
| Aerobic/anaerobic | Aerobic |
| Oxidase | + |
| Catalase | + |
| OF | − |
| Colony color | NP |
| Na$^+$ requirement | + |
| Salt requirement | + |
| Growth on 0% NaCl | − |
| Growth on 1% NaCl | − |
| Growth on seawater | + |
| Substrates utilized | |
| Methanol | − |
| DL-malate | − |
| Glucose | + |
| Main quinone system | Q-8 |
| Mol % (G + C) of intracellular DNA | 44 |

Considering the above characteristics with reference to "Bergey's Manual of Systematic Bacteriology", Krieg, N. R. and Holt, J. G., Vol. 1 (1986), Williams & Wilkins and "Bergey's Manual of Determinative Bacteriology", Holt, J. G., Krieg, N. R., Sneath, P. H. A., Staley, J. T. and Williams, S. T., 9th Edition (1994), Williams & Wilkins, among other reference books, the SHY 1-1 strain was identified to be a microorganism belonging to the genus Alteromonas. However, because of the lack of characteristic colony pigmentation, no species identification could be made.

However, since there was no report about a biojelly-producing strain of microorganism of the genus Alteromonas, the inventors considered the above microorganism to be a novel strain, named it SHY 1-1, and had it deposited with the National Institute of Advanced Industrial Science and Technology (address: AIST Tsukuba Central 6, 1–1, Higashi 1-Chome, Tsukuba-shi, Ibaraki-ken, Japan) under the accession number of FERM BP-7623 (date of deposit: Jun. 1, 2001).

The microorganism according to the invention includes not only said FERM BP-7623 strain but also spontaneous or artificial mutants of FERM BP-7623 and other biojelly-producing strains of microorganisms belonging to the genus Alteromonas.

The above microorganism, when it is incorporated in a coating system and a coating film is formed from the resulting coating on an underwater structure, produces a biojelly in seawater to prevent attachment of macroscopic aquatic life.

Referring to the microorganism to be formulated in a coating, it may be a culture obtained by growing the microorganism in a liquid medium, for instance, or the very microorganism or cells as obtained by centrifugation or other treatment of the culture.

In incorporating the microorganism in a coating system, it is preferable to formulate $10^4$ or more cells per 100 grams of the coating. If the formulating level is below $10^4$ cells, it may happen that, when a coating film is formed, the attachment of macroscopic aquatic life takes place before the microorganism multiplies in seawater to produce a biojelly. The preferred concentration is not less than $10^8$ cells.

The above coating is preferably applied to an underwater structure by means of a roll coater, a brush or the like in a coating thickness of 50 to 2000 μm. The more preferred thickness is 100 to 500 μm.

The method for immobilizing the microorganism in a coating film is not particularly restricted as far as it may allow the microorganism to remain viable in the coating film. Thus, for example, a covalent coupling or other immobilization technique using an insoluble matrix; a crosslinking technique; and a grid, microencapsulation, or other entrapping technique can be employed.

The crosslinking technique mentioned above includes a coating technique using a combination of two or more biopolymers such as polysaccharides (chitin, chitosan, alginic acid, agar, guar gum, etc.) and proteins (milk casein, gelatin, polylysine, polyglutamic acid, etc.); and a coating technique involving crosslinking of one or more biopolymers with a crosslinking agent such as glutaraldehyde.

Furthermore, hydrogels obtainable by utilizing a radical polymerization reaction, such as polyhydroxyethyl methacrylate crosslinked with ethylene glycol dimethacrylate; polyacrylamide crosslinked with bisacrylamide; etc. can also be used.

In the present invention, the form of the coating containing said microorganism is not particularly restricted as far as it is a coating system allowing the microorganism to live but should be selected considering the properties of the reagent to be used for immobilization of the microorganism in the coating film and the compatibility between the reagent and the microorganism, among other. Taking the case in which the coating film-forming material is bisacrylamide-crosslinked polyacrylamide, for instance, because the acrylamide monomer as such is harmful to the microorganism and a mixture of the microorganism and monomer has a poor pot-life at room temperature, it is recommendable to store the microorganism and the film-forming component in independent containers and admix them extemporaneously in the field, that is to say to adopt a two-component or multiple-component system. When a biopolymer such as a polysaccharide and a protein is used as the film-forming component, it is possible to adopt a coating system such that the biopolymer and the microorganism are supplied in one and the same container.

The microorganism of the invention and the coating or coating film utilizing the microorganism can be applied with advantage to underwater structures such as ships and fishnets. Since the microorganism produces a biojelly on underwater structures, it prevents attachment of barnacles, hard-shelled mussels, sea lettuce and so on.

In accordance with the present invention wherein an underwater structure is coated with a coating containing a certain strain of microorganism, a biojelly is produced on the coating film in seawater so that the attachment of macroscopic aquatic creatures such as barnacles, hard-shelled mussels and sea lettuce to the underwater structure can be prevented.

BEST MODE FOR CARRYING OUT THE INVENTION

EXAMPLE 1

Figure 1:
FIG. 1 is a light microphotograph of the SHY 1-1 strain.

The SHY 1-1 strain (FERM BP-7623) was aseptically inoculated into each of the following liquid media 1 to 5 and cultured under static conditions at 30° C. for 1 week.

Referring to media 2 to 5, among the following media, the seawater used was collected from a seashore in Niihama-shi, filtered to remove an insoluble fraction, supplemented with yeast extract, glucose, etc., and sterilized by autoclaving.

Liquid medium 1: Bacto Trypton 10 g/L, yeast extract 5 g/L, NaCl 24 g/L
Liquid medium 2: Seawater only
Liquid medium 3: Seawater, yeast extract 1 g/L
Liquid medium 4: Seawater, glucose 5 g/L
Liquid medium 5: Seawater, yeast extract 1 g/L, glucose 5 g/L After cultivation, each medium was visually observed for growth of the microorganism and formation of a biojelly. As a result, the SHY 1-1 strain was found to have grown well in all the media. Particularly in the case of seawater-basedmedia 2 to 5, an insoluble thin film was observed in the culture broth.

Each culture medium thus obtained was centrifuged and the supernatant was diluted with 3 volumes of ethanol, whereupon white turbidity indicating polysaccharide production developed in all liquid media 1 to 5. Particularly in liquid media 4 and 5 which contained glucose, polysaccharide production was quite prominent.

EXAMPLE 2

The SHY 1-1 strain (FERM BP-7623) was shake-cultured in a liquid medium (Bacto-tryptone 10 g/L, yeast extract 5 g/L, NaCl 24 g/L) at 30° C. for 2 days. The viable count in this culture broth was $3 \times 10_{10}$ cells/ml as measured by the standard plate-counting method. This broth is referred to below as broth A.

Broth A, 1 ml, was mixed with 70 g of 10% aqueous solution of a polyacrylamide having a molecular weight of 13000, 10 g of ethylene glycol dimethacrylate and 0.5 g of ammonium persulfate at 15° C. Then, after addition of 0.2 g of TEMED, the mixture was coated on an acrylic plate and allowed to stand in a nitrogen atmosphere at room temperature for 2 hours. The resulting film is referred to below as coating film 1.

EXAMPLE 3

To 70 g of 3% aqueous solution of alginic acid was added 20 g of 5% aqueous ammonia, followed by stirring. Then, 0.7 ml of broth A and 50 g of 3% aqueous solution of chitosan were added and blended. The resulting composition was coated on an acrylic plate and allowed to stand at room temperature for 3 hours. The resulting film is referred to below as coating film 2.

EXAMPLE 4

40 g of 2-hydroxyethyl methacrylate, 1 ml of broth A, 70 g of 10% aqueous solution of NaCl, 5 g of ethylene glycol dimethacrylate and 0.5 g of ammonium persulfate were mixed at 15° C. Then, after addition of 0.2 g of TEMED, the whole mixture was coated on an acrylic plate and allowed to stand at room temperature in a nitrogen atmosphere for 2 hours. The resulting film is referred to below as coating film 3.

EXAMPLE 5

100 g of 5% aqueous solution of chitosan was mixed with 5 g of NaCl and 1.2 ml of broth A. To this was added 0.5 g of glutaraldehyde, and the whole mixture was coated on an acrylic plate and allowed to stand at room temperature for 3 hours. The resulting film is referred to below as coating film 4.

Comparative Example 1

Except that broth A was not added, a coating film was prepared as in Example 2. This film is referred to below as comparative coating film.

Evaluation of antifouling effect

From the offshore raft of Nippon Paint Co's coastal research institute in Tamano-shi (Seto Inland Sea), the coating films 1 to 4 and comparative coating film were immersed in the water and observed visually for the attachment of macroscopic aquatic life. The results are shown in Table 2. Each figure in the table represents the life attachment area (%).

After 1 month of immersion, biojellies about 2 mm in thickness were observed on coating films 1 to 4.

TABLE 2

| Immersion time | Coating film 1 | Coating film 2 | Coating film 3 | Coating film 4 | Comparative coating film |
| --- | --- | --- | --- | --- | --- |
| 1 Month | 0 | 0 | 0 | 0 | 10 |
| 3 Months | 0 | 0 | 0 | 0 | 100 |
| 6 Months | 0 | 0 | 0 | 0 | 100 |

What is claimed is:

1. A strain of microorganism belonging to the genus Alteromonas growing in seawater, not growing in 1% NaCl, and having the ability to produce a biojelly insoluble in seawater, which is FERM BP-7623.

2. A coating containing the strain of microorganism according to claim 1.

3. A coating film containing the strain of microorganism according to claim 1.

* * * * *

UNITED STATES PATENT AND TRADEMARK OFFICE
CERTIFICATE OF CORRECTION

PATENT NO. : 6,764,846 B2
DATED : July 20, 2004
INVENTOR(S) : Yamamori et al.

It is certified that error appears in the above-identified patent and that said Letters Patent is hereby corrected as shown below:

Column 6,
Line 52, please add the following claims:
   4. (new): A method of preventing attachment of macroscopic aquatic life to an underwater structure which comprises coating the surface of said underwater structure with the coating according to Claim 2.

5. (new): A method of preventing attachment of macroscopic aquatic life to an underwater structure which comprises forming the coating film according to Claim 3 on the surface of said underwater structure.

Signed and Sealed this

Thirtieth Day of November, 2004

JON W. DUDAS
*Director of the United States Patent and Trademark Office*